(12) United States Patent
Yee et al.

(10) Patent No.: US 12,011,147 B2
(45) Date of Patent: Jun. 18, 2024

(54) ACTUATION HANDLE FOR ACCESSORY DEVICES

(71) Applicant: Boston Scientific Scimed, Inc., Maple Grove, MN (US)

(72) Inventors: Catherine Yee, Randolph, MA (US); Shawn Ryan, Littleton, MA (US); Norman May, Valrico, FL (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 73 days.

(21) Appl. No.: 17/455,743

(22) Filed: Nov. 19, 2021

(65) Prior Publication Data

US 2022/0071482 A1 Mar. 10, 2022

Related U.S. Application Data (63) Continuation of application No. 15/357,723, filed on Nov. 21, 2016, now Pat. No. 11,206,968.

(Continued)

(51) Int. Cl.
*A61B 1/00* (2006.01)
*A61B 1/018* (2006.01)
(Continued)

(52) U.S. Cl.
CPC .......... *A61B 1/018* (2013.01); *A61B 1/00087* (2013.01); *A61B 1/00133* (2013.01);
(Continued)

(58) Field of Classification Search
CPC . A61B 1/018; A61B 1/00087; A61B 1/00133; A61B 2017/00296
See application file for complete search history.

(56) References Cited

U.S. PATENT DOCUMENTS 7,094,202 B2 * 8/2006 Nobis ................ A61B 17/2909
                                                              600/101
7,198,599 B2 * 4/2007 Goto .................. A61B 18/1492
                                                              600/154

(Continued)

FOREIGN PATENT DOCUMENTS

CN          101040772 A     9/2007
CN          103037779 A     4/2013

(Continued)

OTHER PUBLICATIONS

(International Search Report and Written Opinion dated Feb. 16, 2017, for PCT/US/ pages).

*Primary Examiner* — Anh Tuan T Nguyen
*Assistant Examiner* — Rynae E Boler
(74) *Attorney, Agent, or Firm* — Bookoff McAndrews, PLLC (57) ABSTRACT

The present disclosure provides an actuation device that comprises: (a) a device body that comprises a first fixation mechanism configured to affix a proximal end of a first elongate member of an accessory device to the device body, (b) an actuator that comprises an operable mechanism and a second fixation mechanism configured to affix a proximal end of a second elongate member of the accessory device to the actuator, wherein the operable mechanism is configured to move the second elongate member relative to the first elongate member, and (c) a fastener configured to attach the device body to an endoscope. The present disclosure further provides endoscopic systems comprising an actuation device of this type in an assembly with an endoscope and an accessory device, and also provides kits that comprise an actuation device of this type and one or more accessory devices.

17 Claims, 5 Drawing Sheets

Related U.S. Application Data (60) Provisional application No. 62/258,107, filed on Nov. 20, 2015.

(51) Int. Cl.
 *A61B 17/00* (2006.01)
 *A61B 17/29* (2006.01)

(52) U.S. Cl.
 CPC .............. *A61B 2017/00296* (2013.01); *A61B 2017/0034* (2013.01); *A61B 2017/2912* (2013.01)

(56) References Cited

U.S. PATENT DOCUMENTS

| | | | |
|---|---|---|---|
| 7,220,227 B2 * | 5/2007 | Sasaki | A61B 1/018 600/102 |
| 8,157,798 B2 * | 4/2012 | Takahashi | A61B 17/072 600/102 |
| 8,197,396 B2 | 6/2012 | Hiraoka | |
| 8,845,516 B2 * | 9/2014 | Chami | A61B 17/12013 600/106 |
| 2005/0119522 A1 * | 6/2005 | Okada | A61B 1/00133 600/153 |
| 2005/0182292 A1 | 8/2005 | Suzuki | |
| 2006/0116692 A1 * | 6/2006 | Ward | A61B 17/00 606/113 |
| 2008/0033238 A1 | 2/2008 | Takahashi | |
| 2008/0161640 A1 | 7/2008 | Weisman | |
| 2009/0259105 A1 | 10/2009 | Miyano et al. | |
| 2011/0099773 A1 | 5/2011 | Golden et al. | |
| 2013/0046297 A1 * | 2/2013 | Lingeman | A61B 17/221 606/41 |
| 2014/0171735 A1 | 6/2014 | Galperin et al. | |
| 2014/0223701 A1 * | 8/2014 | Bean | A61B 1/00066 24/483 |
| 2014/0316203 A1 | 10/2014 | Carroux et al. | |
| 2015/0164307 A1 | 6/2015 | Galperin et al. | |
| 2018/0110404 A1 * | 4/2018 | Devaiah | A61B 1/12 |

FOREIGN PATENT DOCUMENTS

| | | |
|---|---|---|
| CN | 103458813 A | 12/2013 |
| JP | 10751288 A | 2/1995 |
| JP | S11033033 A | 2/1999 |
| JP | 2004049891 A | 2/2004 |
| JP | 2005058749 A | 3/2005 |
| JP | 2005168882 A | 6/2005 |
| JP | 2005198868 A | 7/2005 |
| JP | 2005334132 A | 12/2005 |
| JP | 2007151595 A | 6/2007 |
| JP | 2007325721 A | 12/2007 |
| JP | 2010531712 A | 9/2010 |
| JP | 2014079425 A | 5/2014 |
| WO | 2012106505 A1 | 8/2012 |

* cited by examiner

ACTUATION HANDLE FOR ACCESSORY DEVICES

CROSS REFERENCE TO RELATED APPLICATIONS

This patent application is a continuation of and claims the benefit of priority to U.S. Nonprovisional patent application Ser. No. 15/357,723 filed on Nov. 21, 2016, which claims the benefit of priority to U.S. Provisional Patent Application No. 62/258,107 filed on Nov. 20, 2015, the entireties of which are incorporated herein by reference.

FIELD OF THE INVENTION

The present disclosure generally relates to actuation devices suitable for use in operating accessory devices during an endoscopic procedure.

BACKGROUND

Currently, operators typically often perform endoscopic procedures with the help of assistants to actuate the accessory devices. Ideally, an operator would be able to operate an endoscope while at the same ti e actuating an accessory device.

SUMMARY

In various aspects, the present disclosure pertains to actuation devices suitable for use in operating accessory devices during an endoscopic procedure. The actuation devices comprise: (a) a device body that comprises a first fixation mechanism configured to affix a proximal end of a first elongate member of an accessory device to the device body, (b) an actuator comprising an operable mechanism and a second fixation mechanism configured to affix a proximal end of a second elongate member of an accessory device to the actuator, wherein the operable mechanism is configured to move the second elongate member relative to the first elongate member, and (c) a fastener configured to attach the device body to an endoscope.

In some embodiments, the device body comprises an opening that allows access to a working channel of the endoscope.

In some embodiments, which may be used in conjunction with any of the above aspects and embodiments, the device body may comprise a protrusion that is configured for insertion into a working channel of the endoscope when the device body is attached to the endoscope. In certain of these embodiments, the protrusion may comprise a lumen through which the first and second elongate members of the accessory device can be threaded into the working channel of the endoscope.

In some embodiments, which may be used in conjunction with any of the above aspects and embodiments, the first mechanism may comprise a set screw or clamp and a through hole, the second mechanism ay comprise a set screw or clamp and a through hole or a blind hole, or a combination of both.

In some embodiments, which may be used in conjunction with any of the above aspects and embodiments, the second fixation mechanism may comprise an electrical connector that is configured to electrically connect the second elongate member to an electrical generator.

In some embodiments, which may be used in conjunction with any of the above aspects and embodiments, the fastener may comprise an attachment component that spreads and snaps onto the endoscope.

In some embodiments, which may be used in conjunction with any of the above aspects and embodiments, the device body may be connected to the fastener in a hinged arrangement.

In some embodiments, which may be used in conjunction with any of the above aspects and embodiments, the actuator may be pivotally mounted relative to the device body and the actuator may comprise a lever that can move the actuator around a pivot, such that movement of the lever in a first direction results in retraction of the second elongate member relative to the first elongate member and such that movement of the lever in a second direction opposite the first direction results in advancement of the second elongate member relative to the first elongate member. In certain of these embodiments, (a) the actuator may comprise a projection and the device body may comprise a curved slot within which the projection travels upon rotation of the actuator about the pivot, or (b) the actuator may comprise a first arm that comprises the lever and a second arm that comprises the second fixation mechanism, or (c) the actuation device may further comprise a spring that is configured to bring the actuator to a default position when the lever is released, or (d) a combination of any two or all three of (a), (b) and (c).

In some embodiments, which may be used in conjunction with any of the above aspects and embodiments, the actuator can be set to a plurality of fixed positions within the device body. For instance, the actuator and device body may comprise interlocking stepped ridges, or one of the actuator and the device body may comprise a plurality of depressions and the other of the actuator and the device body may comprise a spring-driven ball that engages the depressions, among other possibilities.

In some embodiments, which may be used in conjunction with any of the above aspects and embodiments, the device body may comprise a port that is configured to allow access for a guidewire.

Other aspects of the present disclosure pertain to endoscopic systems that comprise (a) an endoscope having endoscope controls and a working channel, (b) an actuation device in accordance with any of the above aspects and embodiments, attached to the endoscope through the fastener, and (c) an accessory device that comprises first and second elongate members, the first elongate member being attached to the device body through the first fixation mechanism and the second elongate member being attached to the actuator through the second fixation mechanism. The actuation device may be configured such that, when attached to the endoscope, a single hand of a user can operate both the endoscope controls and operable mechanism of the actuation device.

In some embodiments, which may be used in conjunction with any of the above aspects and embodiments, the first elongate member may be an outer elongate member having a lumen (e.g., in the form of a tube) and the second elongate member may be an inner elongate member (e.g., in the form of a wire or a tube) that is disposed at least partially within the lumen of the outer elongate member.

In some embodiments, which may be used in conjunction with any of the above aspects and embodiments, the accessory device may be fed through the working channel of the endoscope.

In some embodiments, which may be used in conjunction with any of the above aspects and embodiments, the accessory device may be fed alongside the endoscope.

In some embodiments, which may be used in conjunction with any of the above aspects and embodiments, the accessory device may be selected from a knife, a sphincterotome, a snare, an injection device, and forceps.

In some embodiments, which may be used in conjunction with any of the above aspects and embodiments, a cutting member may be attached to a distal end of the second elongate member, such that the cutting member may be exposed upon advancement of the second elongate member relative to the first elongate member, or such that the cutting member may be exposed upon retraction of the second elongate member relative to the first elongate member.

Further aspects of the present disclosure may pertain to kits that comprise (a) an actuation device in accordance with any of the above aspects and embodiments and (b) an accessory device in accordance with any of the above aspects and embodiments.

DETAILED DESCRIPTION

Various particular aspects and embodiments of the disclosure will now be described. As used herein, the term "distal" refers to the end farthest away from a medical professional when introducing a device into a patient, while the term "proximal" refers to the end closest to the medical professional when introducing a device into a patient.

Figure 1A:
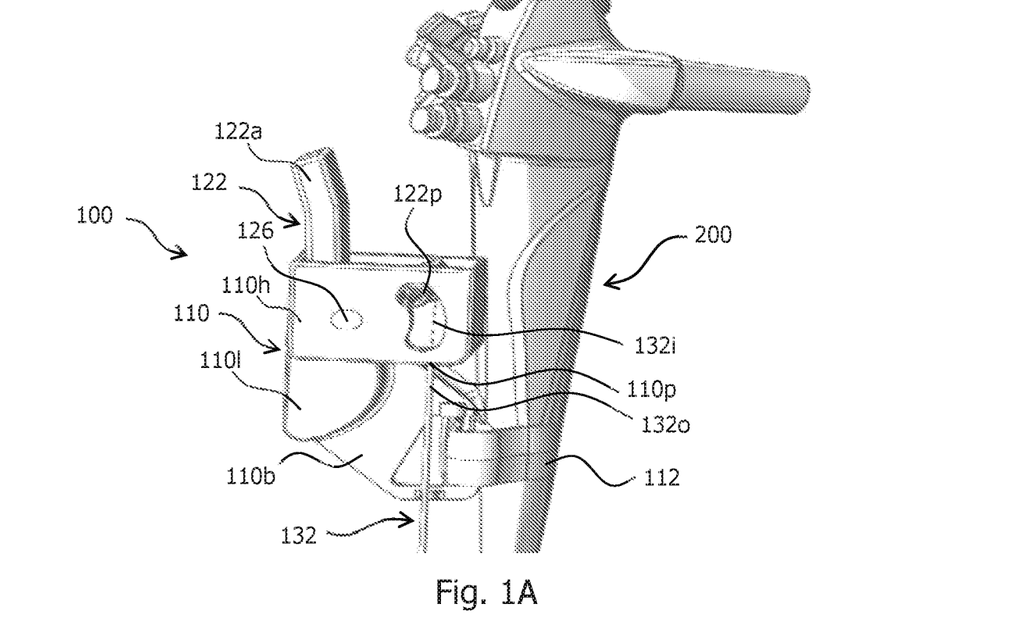
FIGS. 1A and 1B are schematic perspective views showing an endoscope handle, a proximal portion of an accessory device, and an actuation device in accordance with the present disclosure, wherein a lever of the actuation device is placed in two positions for actuation of the accessory device.

With reference now to FIG. 1A, an actuation device 100 is shown in a coupled state with an endoscope 200 and an accessory device 132. The actuation device 100 shown comprises a device body 110, which in the specific embodiment shown includes a housing portion 110h, a bracket portion 110b and a linking portion 110l, which links the housing portion 110h to the bracket portion 110b. The device body 110 further comprises a first connection point 110p where a proximal end of a first elongate member of the accessory device 132, specifically, a hollow outer elongate member 132o (e.g., a catheter) in the particular embodiment shown, is fixed to the body 110. Connection is made via a first attachment mechanism. For example, a through-hole may be formed in the housing portion 110h and a fixation member (e.g., a set screw, clamp, etc.) may be used to fix the proximal end of the hollow outer elongate member 132o within the through-hole.

The actuation device 100 further includes an operable mechanism, specifically, an actuator 122 pivotally mounted relative to the housing portion 110h, in the embodiment shown. The actuator 122 shown comprises a lever 122a that can rotate the actuator 122 around a pivot 126 (e.g., via a pivot pin). The actuator 122 also comprises a second connection point 122p where a proximal end of a second elongate member of the accessory device 132, specifically, an inner elongate member 132i in the particular embodiment shown, is attached to the actuator 122. The inner elongate member 132i is slidably disposed within the outer elongate member 132o of the accessory device 132. The inner elongate member 132i may be solid (e.g., in the form of a wire) or hollow (e.g., in the form of a tube). Connection is made via a second attachment mechanism. For example, a hole (e.g., a blind hole or a through hole) may be formed in the actuator 122 and a fixation member (e.g., a set screw, clamp, etc.) may be used to fix a proximal end of the inner elongate member 132i within the hole. In this way, an operable mechanism may be provided, which is configured to move one elongate member (i.e., an inner elongate member 132i in the embodiment shown) relative to another elongate member (i.e., an outer elongate member 132o in the embodiment shown).

In applications where electrosurgery is required, the actuation device 100 may have an electrically active port so that it can be connected to an electrosurgical generator. In certain of these embodiments, the second attachment mechanism may provide a port for electrical connection to the inner elongate member 132i.

In some embodiments, the actuator 122 may comprise first and second arms, with the first arm corresponding to the lever 122a and the second arm being provided with the second connection point 122p where the proximal end of the inner elongate member 132i of the accessory device 132 is attached to the actuator 122.

In addition to the preceding components, the actuation device 100 may further include a fastener 112 that is configured to attach the device body 110 to the endoscope 200 at a point adjacent to a handle of the endoscope. Examples of fasteners for this purpose include, for instance, straps (e.g., elastic straps, VELCRO hook-and-loop fastener straps, etc.), snap-on clamps, and form fitting grooves, among other possibilities.

Figure 1B:
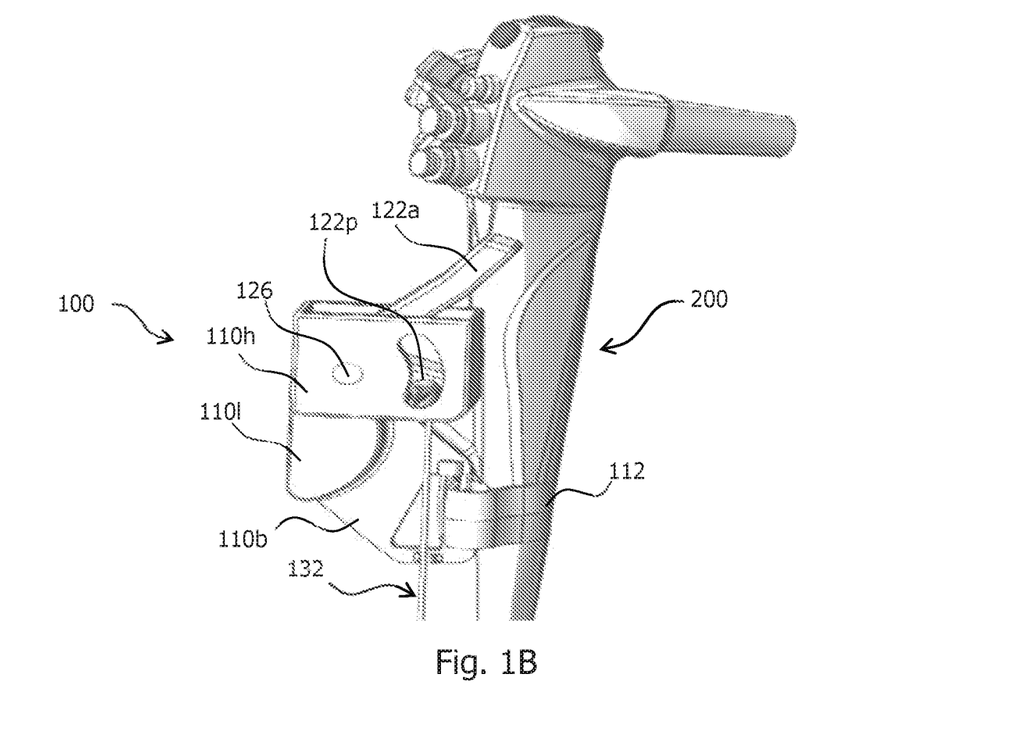

With an arrangement such as that shown in FIGS. 1A and 1B, rotation of the actuator 122 around the pivot 126 and relative to the device body 110 results in movement of the inner elongate member 132i (which is fixed to the actuator 122) relative to the outer elongate member 132o (which is fixed to the device body 110). In the particular embodiment shown, pulling the lever 122a toward the endoscope 200 as shown in FIG. 1B causes the inner elongate member 132i to advance distally relative to the outer elongate member 132o, whereas pushing the lever 122a away from endoscope 200 as shown in FIG. 1A causes the inner elongate member 132i to retract proximally relative to the outer elongate member 132o.

As will be appreciated by those of ordinary skill in the art, the distance that the inner elongate member 132i moves in relation to the outer elongate member 132o is determined by the degree (angle) of rotation of the actuator 122 around the pivot 126 and the distance between the second connection point 122*p* and the pivot 126.

Thus, by affixing the outer elongate member 132*o* to the housing 110*h* of the device body 110 and by affixing the inner elongate member 132*i* that runs within the outer elongate member 132*o* to the pivoting actuator 122, the rotation of the actuator 122 can actuate the desired effect.

Figure 4:
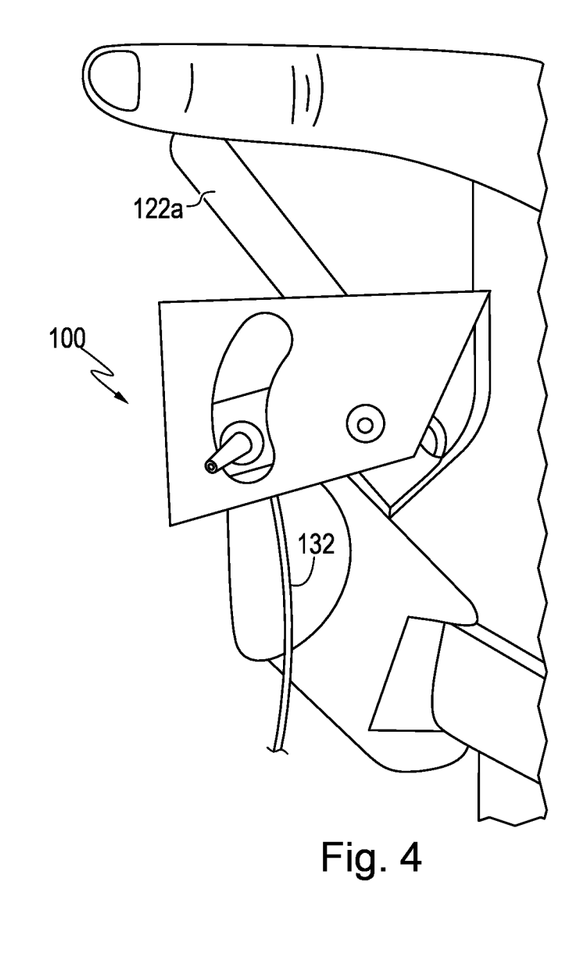
FIG. 4 is a view of a portion of an endoscope handle, a proximal portion of an accessory device and an actuation device, in accordance with the present disclosure.

Although pulling the lever 122*a* in the embodiment shown acts to advance the inner elongate member 132*i* relative to outer elongate member 132*o* and pushing the lever 122*a* retracts the inner elongate member 132*i* relative to outer elongate member 132*o*, one of ordinary skill in the art will appreciate that, in other arrangements, such as that shown in FIG. 4, among others, pulling the lever 122*a* will act to retract the inner elongate member 132*i* relative to outer elongate member 132*o* and pushing the lever 122*a* will act to advance the inner elongate member 132*i* relative to outer elongate member 132*o*. As discussed in more detail below, advancement and retraction of this type may be used to actuate a variety of accessory devices 132 during the course of an endoscopic procedure.

In some embodiments, the actuation device 100 will further comprise a spring or another mechanism that is configured to bring the actuator 122 to a default position when the lever 122*a* is released. For instance, the default position may correspond to an actuator 122 position where the inner elongate member 132*i* is retracted relative to the outer elongate member 132*o*. Alternatively, the default position may correspond to an actuator 122 position where the inner elongate member 132*i* is advanced relative to the outer elongate member 132*o*, or something in between. In one particular example, the default position may correspond to an actuator 122 position where an implement (knife, needle, etc.) disposed at a distal end of the inner elongate member 132*i* is retracted within the outer elongate member 132*o*.

In some embodiments, the actuation device 100 will further comprise a port that is configured to allow access for a guidewire. In applications where a guidewire is used in conjunction with the accessory device 132, a separate guidewire port may be provided in the actuation device 100 to allow access for the guidewire.

In some embodiments, the actuator 122 (and thus the position of the inner elongate member 132*i* relative to the outer elongate member 132*o*) may be set to any of a plurality of different positions. For example, the actuator 122 may be held at a desired position relative to the housing portion 110*h* via a releasable locking mechanism, for instance, by providing the actuator 122 and the housing portion 110*h* with interlocking stepped ridges (e.g., analogous to the complementary ridges of a hemostat). Upon release, the actuator 122 may, in some embodiments, return to a default position via a spring mechanism as discussed above. As another example, the lever actuator 122 may comprise a plurality of depressions and the housing portion 110*h* may comprise a spring-driven ball (e.g., in the form of a ball nose spring plunger, etc.) that engages the depressions, or conversely, the housing portion 110*h* may comprise a plurality of depressions while the actuator 122 may comprise a spring-driven ball that engages the depressions.

Figure 2A:
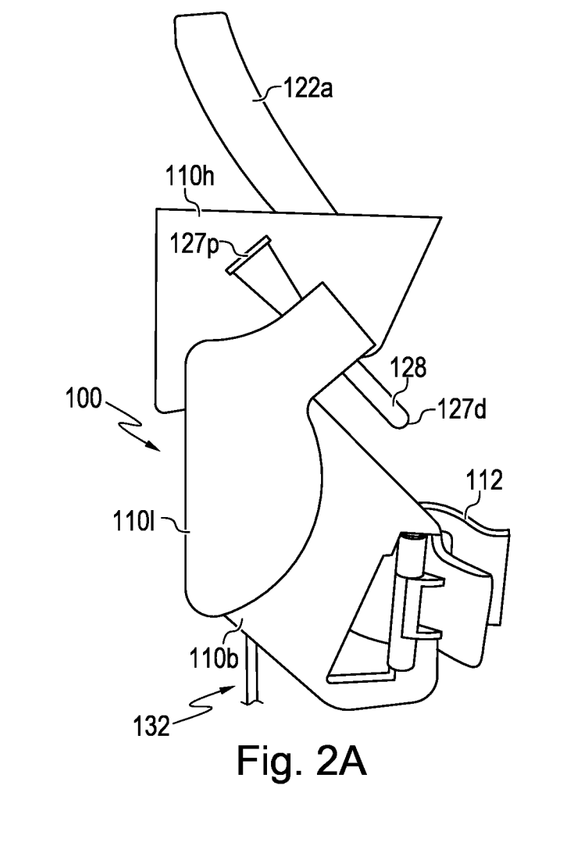
FIGS. 2A and 2B are front and back views of actuation device in accordance with the present disclosure.

Further details of an actuation device 100 like that shown in FIGS. 1A and 1B will now be described in conjunction with FIGS. 2A and 2B. Shown are the components of the device body 110, specifically, the housing portion 110*h*, bracket portion 110*b* and linking portion 110*l*, which are secured to one another and which could readily be formed as a single piece, if desired. As seen from FIG. 2A, the fastener 112 that is configured to attach the device body 110 to the endoscope is in the form of a piece that spreads and snaps onto the endoscope body. The fastener 112 is linked to the bracket 110*b* via a hinge in the embodiment shown, allowing the fastener 112 to hinge around the endoscope body 220. In addition, there is also seen a protrusion 128 that is configured to be inserted into a working channel of the endoscope 200 to which the actuation device 100 is attached. In certain embodiments, an opening will be provided in the actuation device 100, which permits the accessory device 132 access to an endoscope working channel. In the embodiment shown, a lumen extends from a proximal point 127*p* to a distal point 127*d* at a distal end of the protrusion 128, through which the accessory device 132 may be threaded. This arrangement may be further appreciated with the assistance of FIG. 3, which shows the actuation device 100 attached to the endoscope body 220 via the fastener 112. The protrusion 128 is not seen as it is inserted into a port of a working channel 210 of the endoscope, and the accessory device 132 is introduced into the working channel 210 by looping the accessory device 132 into a lumen entrance at point 128*p*. In this way, the accessory device 132 may be looped around from the bottom of the actuation device 100 to the top of the actuation device 100 to enter into the working channel 210, among other possibilities.

Figure 3:
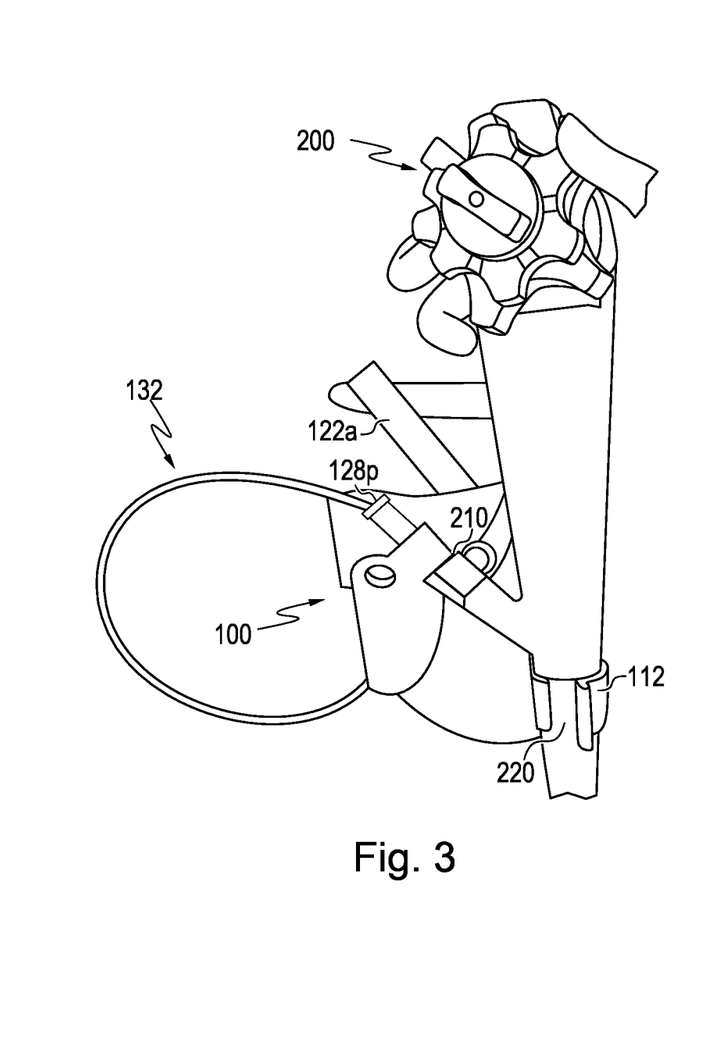
FIG. 3 is a perspective view of an endoscope handle, a proximal portion of an accessory device and an actuation device, in accordance with the present disclosure.

As can be seen from FIG. 3, the actuation device 100 allows an endoscopist to control both the endoscope 200 and the accessory device 132 using one hand. This way, the endoscopist may maneuver and deploy the accessory device 132 without help from an assistant. In this regard, the present disclosure solves the inconvenience of the endoscopist having to depend on an assistant to work the accessory device, thereby allowing the endoscopist full control of the endoscope and accessory device. This way the endoscopist can easily switch between using the features of the endoscope (e.g., water introduction, insufflation, suction, left/right movement, up/down movement, endoscope lock, etc.) and operating the accessory device, single-handedly and comfortably. This also leaves the endoscopists other hand free to continue maneuvering the sheath of the endoscope.

Although the accessory device 132 is routed through the working channel 210 of the endoscope 200 in FIG. 3, in other embodiments, the accessory device 132 may be run alongside the endoscope (e.g., along the length of the endoscope body 220), rather than within a working channel 210 of the endoscope. In these embodiments, the actuation device may be provided with a through-hole or clip for accessory device management. In various embodiments, the accessory device 132 may be longer than the endoscope body 220 to allow the physician to push the accessory device 132 beyond the distal end of the endoscope body and pull it back in as needed.

Figure 2B:
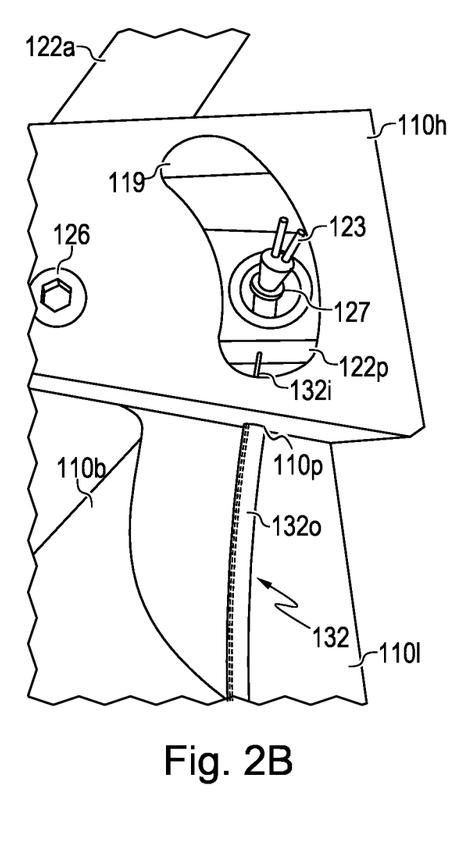

With reference now to FIG. 2B, one can see the housing portion 110*h*, bracket portion 110*b* and linking portion 110*l* of the device body 110. Further shown is the first connection point 110*p* where the proximal end of the hollow outer elongate member 132*o* is fixed to the body 110. Also shown are portions of the actuator 122 that are pivotally mounted relative to the housing portion 110*h*, specifically, the lever 122*a* which is employed to rotate the actuator 122 around the pivot 126 (which in this particular case is in the form of a pivot pin). Also shown is the second connection point 122*p* where the proximal end of the inner elongate member 132*i* (in the form of an actuation wire) is attached. In this particular embodiment, the actuation wire is attached via a 2-in-1 active cord connector 123 which is screwed into a D-block 127 until the actuation wire is fixed in place. Thus, in this embodiment, the connector acts as both a mechanical connector and an electrical connector (e.g., a monopolar electrical connector). Moreover, the connector also forms a protrusion which travels within a slot 119 that is formed in housing 110h. The slot 119 limits the travel of the protrusion and thus the rotation of the actuator within the housing 110h.

Accessory devices which may be actuated by the actuation device of the present disclosure include those that are used in conjunction various procedures including, for example, endoscopic mucosal resection (EMR), endoscopic submucosal dissection (ESD), polypectomy, colonoscopy, transurethral surgery, respiratory surgery, and laparoscopic surgery, among others.

Figure 5A:
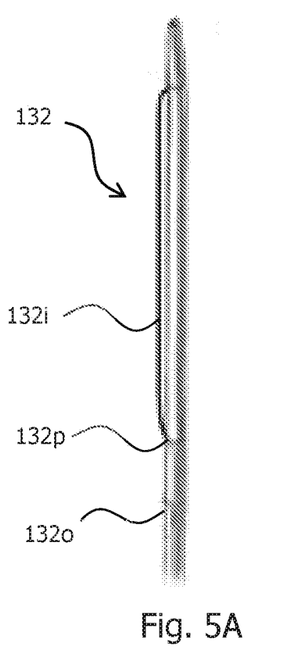
FIGS. 5A and 5B are views of a distal portion of a sphincterotome that is operable using an actuation device in accordance with the present disclosure, wherein the sphincterotome is shown in non-deployed and deployed configurations, respectively.
Figure 5B:
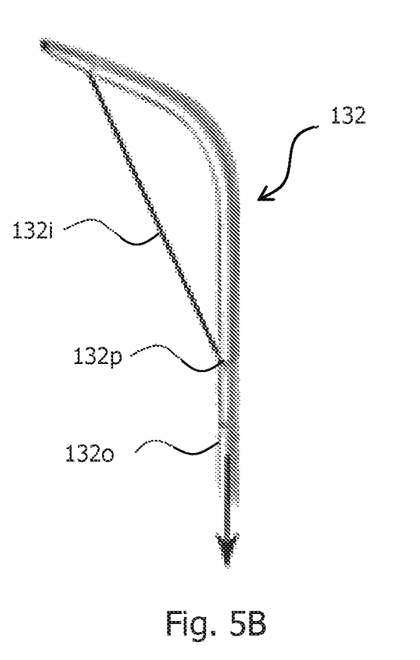

One specific example of an accessory device 132 is a sphincterotome, a distal end of which is illustrated in FIGS. 5A-5B. The sphincterotome 132 includes an outer elongate member 132o (i.e., a catheter) and an inner elongate member 132i (i.e., a pull wire), which emerges from the outer elongate member 132o at a point 132p near its distal end. The outer elongate member 132o and inner elongate member 132i are connected to an actuation device 100 as previously described. When the lever 122a of the actuation device 100 is positioned such that the inner elongate member 132i is distally advanced relative to the outer elongate member 132o, the sphincterotome 132 takes on an orientation like that shown in FIG. 5A. On the other hand, when the lever 122a of the actuation device 100 is positioned such that the inner elongate member 132i is proximally retracted relative to the outer elongate member 132o, the distal tip of the sphincterotome 132 bends as shown in FIG. 5B, exposing the distal end of the inner elongate member 132i, which acts as a cutting wire. Electrical current may be passed through the exposed wire during the cutting process, for example, by establishing a monopolar connection to an electrosurgical generator using an electrical connector as previously described.

If desired the accessory device 132 may be configured such that the default position for the lever is one where the inner elongate member 132i is advanced relative to the outer elongate member 132o, resulting in a default position for the sphincterotome 132 like that shown in FIG. 5A. Such an accessory device 132 may be run alongside an endoscope or be routed through a working channel of the endoscope.

In the preceding example of a sphincterotome, the accessory device 132 is deployed by retracting the inner elongate member 132i relative to the outer elongate member 132o. In other instances, the accessory device 132 is deployed by advancing the inner elongate member 132i relative to the outer elongate member 132o. In this regard, and turning to FIGS. 6A-6B, another example of an accessory device 132 in the form of a cutting knife is shown. The accessory device 132 includes an inner elongate member 132i (i.e., a wire) and an outer elongate member 132o (i.e., a catheter) which are connected at a proximal end (not shown) to an actuation device 100 as previously described. The distal end of the accessory device 132 may be reversibly attached to a distal end 200d of an endoscope via a loop 135 as shown, with the accessory device 132 running outside the endoscope 200, rather than being routed through a working channel of the endoscope, although an analogous accessory device 132 could be routed through the working channel if desired.

Figure 6A:
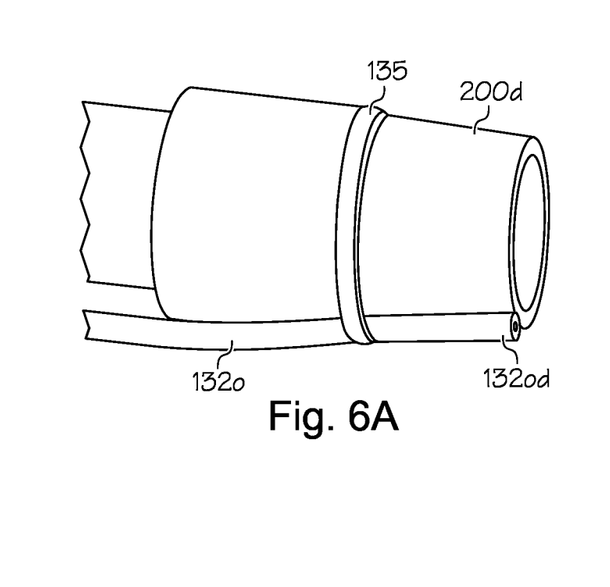
FIGS. 6A and 6B are views of a distal portion of an endoscope and attached cutting knife that is operable using an actuation device in accordance with the present disclosure, wherein the cutting knife is shown in non-deployed and deployed configurations, respectively.
Figure 6B:
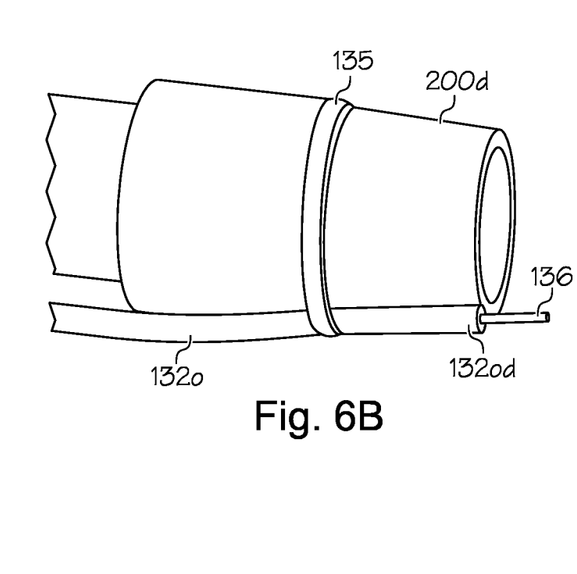

When the lever 122a of the actuation device 100 is positioned such that the inner elongate member 132i is proximally retracted relative to the outer elongate member 132o, the accessory device 132 takes on an orientation like that shown in FIG. 6A. On the other hand, when the lever 122a of the actuation device 100 is positioned such that the inner elongate member 132i is distally advanced relative to the outer elongate member 132o, a cutting knife 136 disposed at a distal end of the inner elongate member 132i extends from the distal end 132od of the outer elongate member 132o as shown in FIG. 6B. Electrical current may be passed through the exposed cutting knife 136 during the cutting process, for example, by establishing a monopolar connection to an electrosurgical generator as previously described.

If desired, the actuation device may be configured such that the default position for the lever 122a is one where the inner elongate r Member 132i is retracted relative to the outer elongate member 132o, resulting in a default position for the accessory device 132 like that shown in FIG. 6A. The act of engaging the lever 122a (e.g., squeezing the lever 122a or pushing the lever 122a, depending on the configuration) will deploy the cutting knife 136 out of the distal end 132od of the outer elongate member 132o, thereby exposing the cutting knife 136 for use. Releasing the lever 122a places the cutting knife 136 into its default retracted position for safety.

In other embodiments, the actuation device 100 may be coupled to an accessory device 132 that comprises an articulating hook or grasper at the distal end. The lever 122a may be used to articulate the distal tool to one side, analogous to the above-described sphincterotome, with the inner elongate member 132i being provided in an off-center position (e.g., in an off-center lumen). In other embodiments, the actuation device 100 may be used to deploy a clip, may be used to deploy a band during EMR, or may be used to deploy a stent. In yet other embodiments, the actuation device 100 may be used to inject a solution, for example, for contrast or for elevation of a lesion, among many other possible applications. In still other embodiments, the actuation device 100 may be used to actuate a snare (including a hot snare) or to actuate hot or cold biopsy forceps. In still other embodiments, the actuation device 100 may be used to actuate a catheter (e.g., Alair™ Bronchial Thermoplasty system, Boston Scientific Corporation, Marlborough Mass.), a medical laser probe (e.g., thulium laser system) or mechanical scissors.

In some embodiments, the actuation device may be manufactured to be universal, so that different accessory devices may be easily attached to it. That way when the physician is switching tools, the handle can be left in place while the accessory tool is swapped.

While the devices, assemblies and methods of this disclosure have been described in terms of preferred embodiments, it may be apparent to those of skill in the art that variations can be applied without departing from the concept, spirit and scope of the disclosure. All such similar substitutes and modifications apparent to those skilled in the art are deemed to be within the spirit, scope and concept of the disclosure as defined by the appended claims.

The invention claimed is:

1. An actuation device comprising:
a device body that comprises a first fixation mechanism configured to affix a proximal end of a first member of an accessory device to the device body and a portion configured to be coupled to a working channel of a medical device, wherein the portion defines a lumen; and
an actuator comprising an operable mechanism, a second fixation mechanism configured to affix a proximal end of a second member of the accessory device to the actuator, wherein the second member extends through an interior of the first member, wherein movement of the operable mechanism from a first position to a second position is configured to move the second member distally relative to the first member, and movement of the operable mechanism from the second position to the first position is configured to move the second member proximally relative to the first member,
wherein the operable mechanism pivots about a point offset from a longitudinal axis of the first member and the second member,
wherein the second fixation mechanism is configured to move from a first end of a curved path to a second end of the curved path, and wherein a distance from the first end to the second end defines a maximum distance the second member is configured to move relative to the first member, and
wherein, in a configuration in which the portion of the device body is coupled to the working channel of the medical device:
  a first portion of the first member and a first portion of the second member extend through the lumen of the portion,
  a second portion of the first member and a second portion of the second member are both external to the device body and the actuator, wherein the second portions of the first and the second members are proximal of the respective first portions of the first and the second member, and
  a third portion of the first member and a third portion of the second member extend into the working channel of the medical device, wherein the third portions of the first and the second members are distal to the respective first portions of the first and the second member.

2. The actuation device of claim 1, wherein the device body comprises an opening that allows access to the working channel of the medical device, and wherein the device body comprises a port that is configured to allow access for a guidewire.

3. The actuation device of claim 1, wherein the medical device is an endoscope, wherein the portion comprises a protrusion that is configured for insertion into the working channel of the endoscope, and wherein the protrusion defines the lumen.

4. The actuation device of claim 1, further comprising a fastener configured to attach the actuation device to the medical device, wherein the fastener includes an attachment component that spreads and snaps onto the medical device.

5. The actuation device of claim 1, wherein the actuator is pivotally mounted relative to the device body, and wherein the actuator comprises a lever that can move the actuator around a pivot.

6. The actuation device of claim 1, wherein the actuator can be set to a plurality of fixed positions within the device body.

7. The actuation device of claim 1, wherein the first fixation mechanism comprises a set screw or clamp and a through hole, wherein the second fixation mechanism comprises a set screw or clamp and a through hole or a blind hole, or both.

8. The actuation device of claim 1, wherein the second fixation mechanism comprises an electrical connector that is configured to electrically connect the second member to an electrical generator.

9. The actuation device of claim 1, further comprising a biasing member configured to bias the actuator in the first position, wherein the operable mechanism is configured to move from the first position to the second position in response to the operable mechanism receiving a force sufficient to overcome a force of the biasing member.

10. The actuation device of claim 9, wherein a proximal end of the actuator is pivotally mounted to the device body, and wherein a distance between a distal end of the actuator and the medical device fastened to the actuation device decreases as the actuator moves from the first position to the second position.

11. The actuation device of claim 1, further comprising a fastener, wherein the fastener includes a hinge having a hinge axis of rotation that is parallel to an extension direction of the medical device attached to the actuation device, and wherein the hinge is configured to rotate the device body about the hinge axis of rotation.

12. An endoscopic system comprising:
an endoscope having a handle with endoscope controls, and a working channel; and
an actuation device removably attached to the handle of the endoscope and comprising:
  a device body that comprises a first fixation mechanism configured to affix a proximal end of a first member of an accessory device to the device body; and
  an actuator comprising (a) a lever coupled to an operable mechanism and (b) a second fixation mechanism configured to affix a proximal end of a second member of the accessory device to the actuator, wherein the operable mechanism is configured to move the second member relative to the first member, wherein the second fixation mechanism is configured to move from a first end of a curved path to a second end of the curved path opposite the first end, wherein a free end the lever, opposite an axis of rotation of the lever and free from coupling to any other portion of the actuation device, extends proximally of a proximalmost end of the device body;
wherein, in a configuration in which the second fixation mechanism is at the first end of the curved path, the lever has a first angle relative to a longitudinal axis of the handle of the endoscope, wherein the longitudinal axis of the handle extends from a proximal end of the handle to a distal end of the handle, wherein, in a configuration in which the second fixation mechanism is at the second end of the curved path, the lever has to a second angle relative to the longitudinal axis of the handle, wherein movement of the lever from the first angle to the second angle moves the second member relative to the first member, and wherein a distance from the first end of the curved path to the second end of the curved path defines a maximum distance the second member is configured to move relative to the first member, and
wherein the actuation device is configured such that a single hand of a user can operate both the endoscope controls of the handle and the lever of the actuation device.

13. The endoscopic system of claim 12, wherein the first member is an outer member having a lumen, and wherein the second member is an inner member that is disposed at least partially within the lumen of the outer member.

14. The endoscopic system of claim 12, wherein the accessory device is fed through the working channel of the endoscope, and wherein the accessory device is selected from a knife, a sphincterotome, a snare, an injection device, and forceps.

15. The endoscopic system of claim 12, wherein a cutting member is attached to a distal end of the second member, and wherein the cutting member is exposed upon advancement of the second member relative to the first member, or wherein the cutting member is exposed upon retraction of the second member relative to the first member.

16. The actuation device of claim 1, wherein both the second portion of the first member and the second portion of the second member form a loop.

17. The endoscopic system of claim 12,
wherein the device body further comprises a portion configured to be removably coupled to the working channel of the endoscope, wherein, in a configuration in which the portion of the device body is coupled to the endoscope:
a first portion of the first member and a first portion of the second member extend through a lumen of the portion,
a second portion of the first member and a second portion of the second member are both external to the device body and the actuator, wherein the second portions of the first and the second members are proximal of the respective first portions of the first and the second member, and
a third portion of the first member and a third portion of the second member extend into the working channel of the endoscope, wherein the third portions of the first and the second members are distal to the respective first portions of the first and the second member.

\* \* \* \* \*